US011452531B2

(12) United States Patent
Ahrens et al.

(10) Patent No.: US 11,452,531 B2
(45) Date of Patent: Sep. 27, 2022

(54) SURGICAL CUTTING INSTRUMENT

(71) Applicant: Spinal Stabilization Technologies, Dublin (IE)

(72) Inventors: Michael Ahrens, Neustadt (DE); Ralph Duerr, Neuhausen (DE)

(73) Assignee: SPINAL STABILIZATION TECHNOLOGIES, Dublin (IE)

( * ) Notice: Subject to any disclaimer, the term of this patent is extended or adjusted under 35 U.S.C. 154(b) by 393 days.

(21) Appl. No.: 16/482,861

(22) PCT Filed: Jan. 12, 2018

(86) PCT No.: PCT/EP2018/050782
§ 371 (c)(1),
(2) Date: Aug. 1, 2019

(87) PCT Pub. No.: WO2018/141533
PCT Pub. Date: Aug. 9, 2018

(65) Prior Publication Data
US 2020/0229829 A1    Jul. 23, 2020

Related U.S. Application Data

(60) Provisional application No. 62/453,146, filed on Feb. 1, 2017.

(30) Foreign Application Priority Data

Feb. 1, 2017    (EP) .................................... 17154264

(51) Int. Cl.
*A61B 17/16*      (2006.01)
*A61B 17/295*     (2006.01)
(Continued)

(52) U.S. Cl.
CPC ...... *A61B 17/1671* (2013.01); *A61B 17/1606* (2013.01); *A61B 17/295* (2013.01);
(Continued)

(58) Field of Classification Search
CPC ............ A61B 17/1604; A61B 17/1606; A61B 17/1608; A61B 17/1611; A61B 17/1671; A61B 17/1659; A61B 17/16–17/1697
See application file for complete search history.

(56) References Cited

U.S. PATENT DOCUMENTS 2,568,234 A * 9/1951 Haufrect ............ A61B 17/3201
                                                606/174
5,827,323 A * 10/1998 Klieman ............ A61B 17/2909
                                                606/205
(Continued)

FOREIGN PATENT DOCUMENTS

EP    2241273 A1 * 10/2010    ......... A61B 17/1608
EP    2241273 A1    10/2010

OTHER PUBLICATIONS

International Search Report; priority document.

*Primary Examiner* — Zade Coley
(74) *Attorney, Agent, or Firm* — Greer, Burns & Crain, Ltd.

(57)    ABSTRACT

A surgical cutting instrument (3) having a proximal end (4), a distal end (5), opposing sides (6, 7), and a longitudinal axis (8) and comprising: (i) an instrument body (2); (ii) a pivotal cutting arm (10) having a pinion (20) with an axis of rotation, the pinion being integrally formed with the pivotal cutting arm, wherein the pivotal cutting arm is mounted for rotation relative to the instrument body about a pivot axis (11), the pivot axis being the axis of rotation of the pinion, so that, rotation of the pinion about the pivot axis, causes the pivot arm to pivot relative to the instrument body; (iii) a cutting blade (40) on the pivotal cutting arm for resecting (Continued)

tissue; (iv) a rack (25) that can be moved in a reciprocating linear motion forward towards the distal end and rearwards toward the proximal end, the rack and the pinion being meshed together to forming a rack and pinion mechanism so that linear motion of the rack effects pivotal movement of the pivotal cutting arm about the pivot axis. This provides a very simple yet robust device which can have a minimum cross-section. It can thus be used for minimally invasive procedures such as cutting material from the interior of a spinal disc.

15 Claims, 4 Drawing Sheets

(51) Int. Cl.
*A61B 17/00* (2006.01)
*A61B 17/29* (2006.01)
*A61B 17/32* (2006.01)

(52) U.S. Cl.
CPC ............... *A61B 2017/00261* (2013.01); *A61B 2017/00473* (2013.01); *A61B 2017/2931* (2013.01); *A61B 2017/2943* (2013.01); *A61B 2017/32006* (2013.01)

(56) References Cited

U.S. PATENT DOCUMENTS

| | | | | |
|---|---|---|---|---|
| 5,836,958 | A * | 11/1998 | Ralph | A61B 17/1671 606/160 |
| 2002/0173813 | A1* | 11/2002 | Peterson | A61B 17/1604 606/167 |
| 2013/0238006 | A1* | 9/2013 | O'Neil | A61B 17/32 606/170 |
| 2016/0008141 | A1* | 1/2016 | Huffmaster | A61B 17/320016 623/17.16 |

* cited by examiner

SURGICAL CUTTING INSTRUMENT

CROSS REFERENCES TO RELATED APPLICATIONS

This application is a United States National Stage Application under 35 U.S.C. Section 371 of International Patent Application No. PCT/EP2018/050782 filed on Jan. 12, 2018, claiming priority to European Patent Application No. 17154264.0 filed on Feb. 1, 2017 and U.S. Provisional Patent Application No. 62/453,146 filed on Feb. 1, 2017, all of which are hereby incorporated by reference as if fully set forth herein.

FIELD OF THE INVENTION

The present invention relates to surgical cutting instruments.

BACKGROUND TO THE INVENTION

Surgical cutting instruments are well known. Specific surgical cutting instruments are configured for use in specific medical applications/procedures.

Surgical instruments need to be robust. They often experience considerable forces in use. On the other hand, the trend in surgery is towards minimally invasive methods. It is difficult to balance these requirements because reduction in size of surgical instruments reduces the strength of the instrument.

For example, in the case of a surgical cutting instrument that is for use in performing cuts in a spinal disc, it is desirable to have an instrument of a minimum cross sectional area as this has a requirement for a lesser invasive or disruptive access.

International Patent Publication No. WO 02/096306 describes a tool for cutting tissue within a spinal disc which has a mechanism for rotating a cutting arm relative to the instrument body. It has a relatively complex linkage mechanism for rotating the cutting arm. The cutting action in this device has significant alternating forces and speeds of the movement with peaks forces at the end and beginning of the cutting movement. This is undesirable.

Notwithstanding the foregoing, it is desirable to provide an alternative surgical cutting instrument that is robust, reliable in use, and can be constructed with a relatively small cross sectional area which allows it to be used in surgical applications with minimal invasiveness.

SUMMARY OF THE INVENTION

In one aspect, the present invention provides a surgical cutting instrument having a proximal end, a distal end, opposing sides, and a longitudinal axis and comprising:
(i) an instrument body;
(ii) a pivotal cutting arm having a pinion with an axis of rotation, the pinion being integrally formed with the pivotal cutting arm, wherein the pivotal cutting arm is mounted for rotation relative to the instrument body about a pivot axis, the pivot axis being the axis of rotation of the pinion, so that, rotation of the pinion about the pivot axis, causes the pivot arm to pivot relative to the instrument body;
(iii) a cutting blade on the pivotal cutting arm for resecting tissue;
(iv) a rack that can be moved in a reciprocating linear motion forward towards the distal end and rearwards toward the proximal end, the rack and the pinion being meshed together to forming a rack and pinion mechanism so that linear motion of the rack effects pivotal movement of the pivotal cutting arm about the pivot axis.

A surgical instrument of the invention can circumferentially resect target areas such as within a disc space of a spinal disc.

A surgical cutting instrument of the invention can be made with a relatively low profile, for example the instrument body (at least that part of the instrument body that is for insertion into a subject) and the cutting arm desirably have a profile with a cross sectional area with a diameter no greater than about 7 mm.

These are small dimensions allowing for minimum invasiveness. Yet the surgical cutting instrument of the present invention is very robust and can withstand the relatively high forces experienced.

The surgical cutting instrument of the present invention allows for linear and/or constant force transmission from a user to the cutting arm. This is important for control and safety and effectiveness of the cutting action.

The rack and pinion mechanism is a mechanism for pivoting the cutting blade, which is desirably a u-shaped blade, relative to the instrument body. The rack is a toothed rack. The teeth of the pinion and those of the rack mesh with each other.

The axis of rotation is desirably located intermediate the proximal end and the distal end.

Desirably the cutting arm is pivotally mounted on a support which has a forward support portion which extends forwardly towards the distal end and a rearward support portion which extends rearwardly toward the proximal end. The support can be used for location of the device correctly at a target site. Also, it can provide a surface against which the cutting action can be affected, for example by preventing movement of tissue pressed against it by the cutting arm. In this respect it can form an anvil type form. Indeed because the blade rotates through an angular range of movement it is desirable that both the forward support surface and the rearward support surface take the form on an anvil. This means an anvil is available when the cutting arm is cutting by rotating in two opposing directions about its axis of rotation.

The axis of rotation is desirably located intermediate the proximal end and the distal end and above the support.

The pinion takes the form of a sector of a gear wheel.

Desirably together the support surface and the cutting arm desirably have a profile with a cross sectional area with a diameter no greater than about 7 mm. As the cutting arm can moved, it will be appreciated that references to the cross-sectional area including the cutting arm refers to a position of the cutting arm which gives the minimum cross sectional area.

The support may have a channel defined therein and desirably the rack can be moved in a reciprocating linear motion forward towards the distal end and rearwards toward the proximal end within the channel. Adding the channel within the support, and having the cutting arm mounted on the support, allows for ease of meshing of the pinion on the cutting arm with the rack. This is also a very mechanically robust arrangement.

The push and pull movement which results from the provision of the rack and pinion mechanism results in an equal cutting ability in different orientations and also allows for cutting by rotation in two opposing directions. For example a first cut may be made by moving the arm from a first position to a second position using the rack and pinion mechanism. Then, a second cut can be made by moving the arm from the second position back towards a first position. Optionally the device can be turned through 180 degrees between the first and second cut thus allowing a continuous block to be cut out by circumferential cutting.

The pivotal cutting arm may be pivotally mounted to the instrument between two brackets located on opposing sides of the instrument. For example where the support has a channel defined therein suitably the brackets are on opposite sides of the channel. Optionally the rack can be moved in a reciprocating linear motion forward towards the distal end and rearwards toward the proximal end within the channel.

Again this is a simple robust arrangement which allows a strong device to be formed yet which has a minimum cross sectional profile.

A surgical cutting instrument of the invention may optionally further comprise a worm screw that meshes with the rack so as to form a worm drive that effects movement of the rack. Again this is a very simple yet strong construction.

The worm screw is at the end of a rotatable shaft and is optionally integrally formed with the rotatable shaft. Rotation of the rotatable shaft will effect rotation of the worm screw. Such mechanism can be provided with a profile that has a relatively small diameter in cross-sectional area.

Desirably the rearward support portion has an opening on an upper surface thereof and the rack extends into the rearward support portion. Optionally the worm drive extends into the rearward support portion too.

There is thus a cutting head on the instrument body at the distal end of the instrument.

The cutting blade may be an annular blade (with an open centre) and is desirably elongate with a major axis and a minor axis. The blade may extend about the perimeter of the annular blade.

The cutting arm is a rigid arm. The surgical instrument is for performing a circular cut in spinal disc tissue with the main purpose of preparing the inner space of a spinal disc during a total nucleus removal (TNR) as part of a nucleus replacement procedure. The surgical cutting instrument of the invention allows for ease of making a predictable cut in tissue. For example, it can be used to prepare the inner portion (nucleus) of a disc in a predicable manner by conducting a circular cut through the nucleus and annulus thus resecting a predefined shape and volume.

The surgical cutting instrument of the invention does not remove the material. It makes a cut. The cut material cut then be removed with another instrument for example a rongeurs. In the case of a spinal disc the overall result is a geometrical void in the inner disc. For safety reasons and optimal fitting implant spinal disc interface regular predictable cutting of a predefined shape is a desired result.

The cutting arm cuts through the material and does not collect it or remove it. The cut material passes completely through the cutting arm. During cutting the material passes from one side of the cutting arm out through the centre of the cutting arm to a position where it is on the other side of the cutting arm. The cutting arm of the invention thus passes completely through the material leaving the cut material behind in situ. As the cut material has been separated by the cutting action it can be later removed. This applies to all cutting arms of the invention whether u-shaped or annular. All have an open centre. The cut material completely passes through the open centre of the cutting arm. A continuous block of cut material is left behind in-situ for later removal.

A surgical cutting instrument of the invention can be made with a relatively low profile, for example the instrument body (at least that part of the instrument body that is for insertion into a subject) and the cutting arm desirably have a profile with a cross sectional area with a diameter no greater than about 7 mm.

If at least part of the instrument body is considered to be a shaft then the diameter of the shaft and the cutting head can be the same, preferably less than 7 mm.

A locating mechanism may be provided for releasably locating the device in place, when in use during surgery, relative to the anatomical part on which it is being used.

The cutting blade may be a u-shaped blade having two sides joined by a bridging portion and the bridging portion allows relative movement of the sides so that the shape of the blade is adjustable. This means blocks of tissue can be cut out to different shapes.

Any blade may be made of flexible material (metal, plastic, ceramics, composite or combination thereof) allowing change of form and orientation of blade for adaptation to individual anatomy for example anatomy such as the concave endplates of a spinal disc.

A blade may have a hinge, for example a live hinge, to allow change of shape of the blade. For example a blade may have two parts hinged together to allowing for change of shape of the blade.

A guide forming a visual aid may be employed to ensure that the surgical cutting instrument of the present invention is correctly aligned relative to the target site, for example parallel to the endplates of a spinal disc rather than being arranged at an offset angle thereto. It will be appreciated that if a device is offset from its correct orientation it may not make the desired cut or may cut into tissue which it is not desired to cut. For example a spirit level type arrangement or an electronic indicator may be used.

A surgical cutting instrument of the present invention may include a protection runner that moves with the cutting arm, so that in use it spaces the cutting blade away from any surface the protection runner runs across. For example it may prevent the blade from cutting into cartilage or bone within a spinal disc. A protection runner may be provided on one but desirably each opposing outer sides of the cutting blade so that the blade is held away from a surface. The protection runner may be a protrusion e.g. a rounded protrusion protruding from an outer side of the blade. It may be integrally formed with a blade. A protection runner will not extend up to the cutting edge of the blade but rather is spaced (to follow) a distance from a cutting edge. In the case of a two-sided or double action blade the protection runner(s) is desirably spaced from both cutting edges for example equidistant from each and centred between them.

A surgical cutting instrument of the invention may include a releasably attachable surgical instrument head so that a first surgical instrument head can be swapped for another on the instrument body. This allows for interchange of identical surgical instrument head, for example to avoid contamination between repeated use, and also to allow different head to be used. For example different cutting arms and/or a different blades may be desired for different target sites.

Desirably the first releasably attachable surgical instrument head comprises:
  (i) the pivotal cutting arm;
  (ii) the pinion; and
  (iii) the cutting blade.

Optionally the first releasably attachable surgical instrument head further includes the rack.

Optionally the first releasably attachable surgical instrument head further includes the worm screw.

Upon attaching the releasably attachable surgical instrument head to the instrument body the surgical instrument head and the instrument body automatically engage with each other. For example a bayonet type fitting may be used for a click on mechanism for the purposes of engaging the two parts.

Where the releasably attachable surgical instrument head includes the rack it is desirable that the rack automatically engages with the remainder of the instrument body so as be moveable.

Where the releasably attachable surgical instrument head includes the worm screw it is desirable that it is already interengaged with the rack. The worm screw then automatically engages with a shaft that rotates it.

The surgical instrument body is thus reusable whereas the releasably attachable surgical instrument head may be only used once.

BRIEF DESCRIPTION OF THE DRAWINGS

Embodiments of the invention will be described, by way of example only, with reference to the accompanying drawings in which.

DETAILED DESCRIPTION OF THE DRAWINGS

Figure 1:
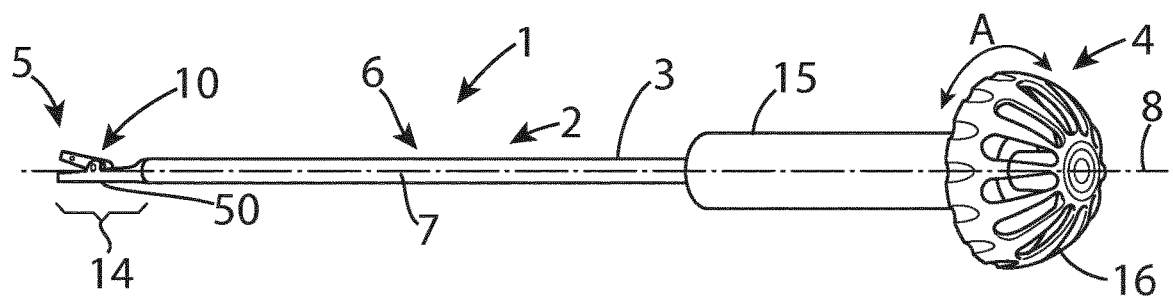
FIG. 1 is a perspective view from one side of a surgical cutting instrument of the invention with a cutting arm in a pivoted position relative to a longitudinal axis of the surgical cutting instrument.

As shown in FIGS. 1 to 12, the present invention provides a surgical cutting instrument 1 having an instrument body 2 which, as is desirable in all embodiments, is an elongate hollow body or tube 3. The surgical instrument body 2 has a proximal end 4 which is typically held by a user, and a distal end 5, which is for insertion into a subject for cutting/resection of tissue. The surgical instrument body 2 has opposing sides, which, from the perspective of a user looking from the proximal end towards the distal end takes the form of a right side 6 and a left side 7. The surgical instrument body 2 has a longitudinal axis 8. All surgical instruments of the invention will be elongate in the orientation in which they are for insertion into a subject.

A pivotal cutting arm 10 is mounted for rotation relative to the instrument body 2 about a pivot axis 11. The pivot axis 11 is perpendicular to the longitudinal axis 8 of the surgical instrument body 2.

The cutting arm 10 has a u-shaped blade 40 thereon. The u-shaped blade 40 has two sides, a right side 41 and a left side 42 which are joined by a bridging portion 43. The blade 40 is flexible and can be bent into various different shapes and in particular shaped for the cutting task in hand. Some exemplary shapes are shown in FIGS. 9(A) to 9(D). For example the bridging portion 43 can act a (live) hinge (see the circled part of the blade in FIG. 9(B)) allowing movement of the sides so that the shape of the blade is adjustable.

Figure 3:
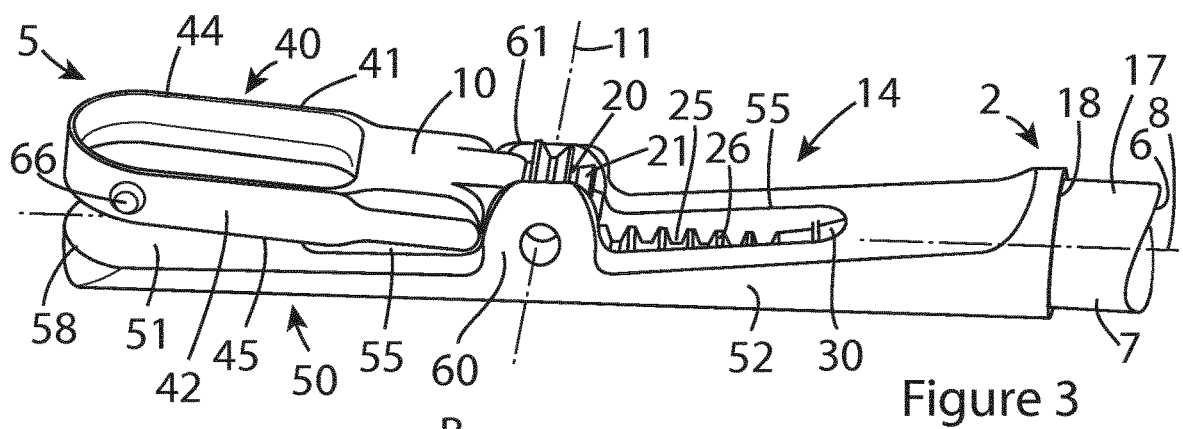
FIG. 3 shows an enlarged partial perspective view from one side of a releasably attachable surgical instrument head of the surgical cutting instrument of the type shown in FIG. 1 with a cutting arm pivoted at a small angle similar to the position shown in FIG. 1.
Figure 4:
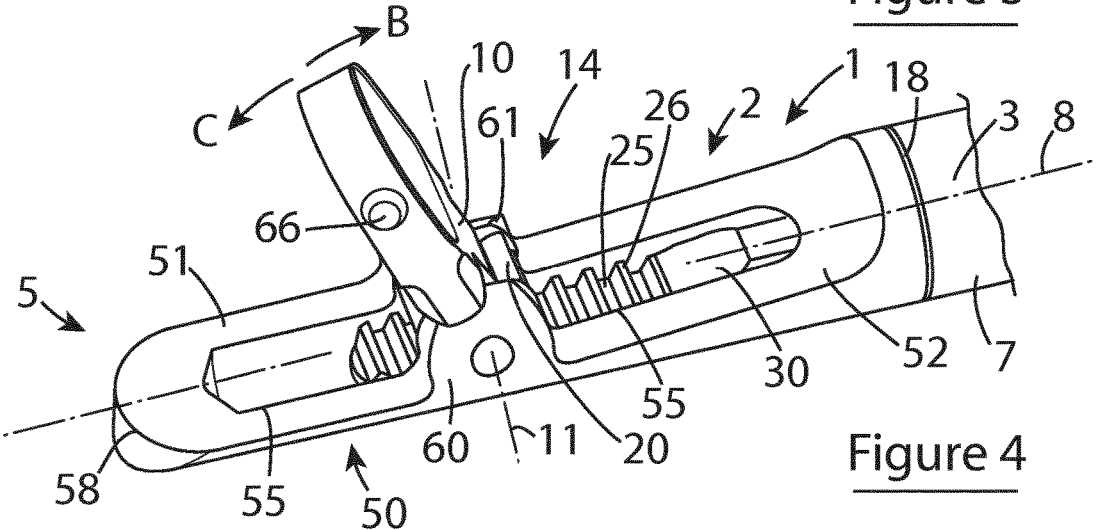
FIG. 4 shows an enlarged partial perspective view from one side of a surgical cutting instrument of the type shown in FIG. 1 with a cutting arm pivoted at a larger angle relative to the position shown in FIG. 1.

The blade 40 can have cutting edges on both an upper periphery 44 and a lower periphery 45 thereof as best seen in FIG. 3. It can thus cut when being moved in opposing rotational directions for example in the direction of Arrow B or the direction of Arrow C (see FIG. 4).

The cutting arm 10 is pivotally mounted on a support 50 which has a forward support portion 51 which extends forwardly (relative to the pivot position of the cutting arm 10) towards the distal end 5 and a rearward support portion 52 which extends rearwardly (relative to the pivot position of the cutting arm 10) toward the proximal end 4. In this respect the support 50, and in particular each of the support portions 51 and 52 have an anvil type form where cutting of tissue can be effected by the blade cutting through tissue that is prevented from moving away from the device by the support portions 51 and 52. Because the blade 40 rotates through an angular range of movement it is desirable that both the forward support surface 51 and the rearward support surface 52 take the form on an anvil. This means an anvil is available when the cutting arm is cutting by rotating in two opposing directions about its axis of rotation. There is then blade against anvil action available in one or both directions to assist with cutting of tissue.

When the cutting arm 10 is abutting the support 50 (see the position in FIG. 2 and the position in FIG. 5) the cutting arm 10 together with the support 50 together have a profile which is no greater in cross-sectional area than the surgical instrument body 2. The surgical instrument body 2 and the cutting arm 10 each desirably have a profile with a cross sectional area with a diameter no greater than about 7 mm. These are small dimensions allowing for minimum invasiveness. Yet the surgical cutting instrument of the present invention is very robust and can withstand the relatively high forces experienced.

The pivotal cutting arm 10 is pivotally mounted to the instrument 1, and in particular the support 50 between two brackets 60,61 located on the support 50 and on opposing sides 6,7 of the instrument 1. In particular the brackets 60,61 are on opposite sides of the channel 55.

The surgical cutting instrument 1 has a grip portion 15 and a rotatable knob 16. The surgical instrument body 2 desirably has a profile with a cross sectional area with a diameter no greater than about 7 mm for that portion of the device that will be inserted into a subject. In the present case the grip 15 is to be held by a user and that part of the device remains outside a subject when in use. Accordingly the grip can have a profile with a cross sectional area that is much greater than 7 mm.

Figure 2:
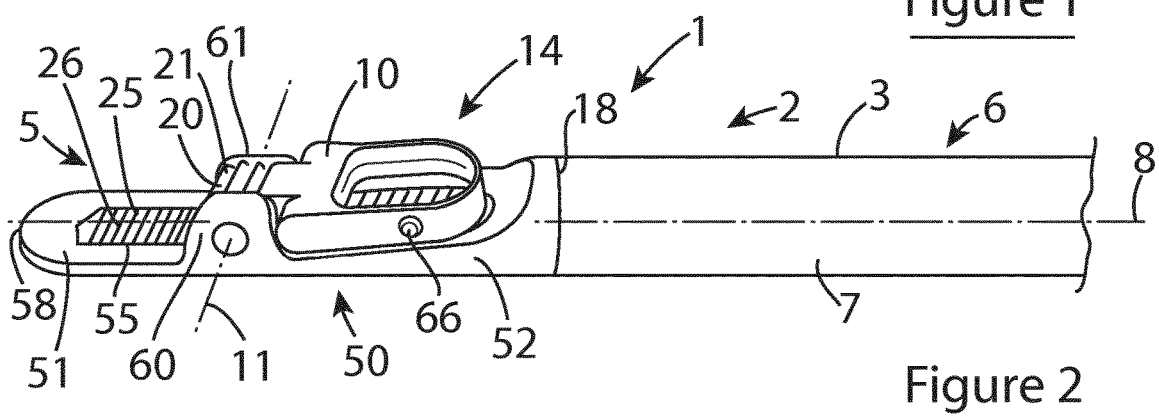
FIG. 2 is an image showing a partial perspective view from one side of a surgical cutting instrument of the type shown in FIG. 1 with a cutting arm pivoted approximately 180 degrees relative to the position shown in FIG. 5.
Figure 5:
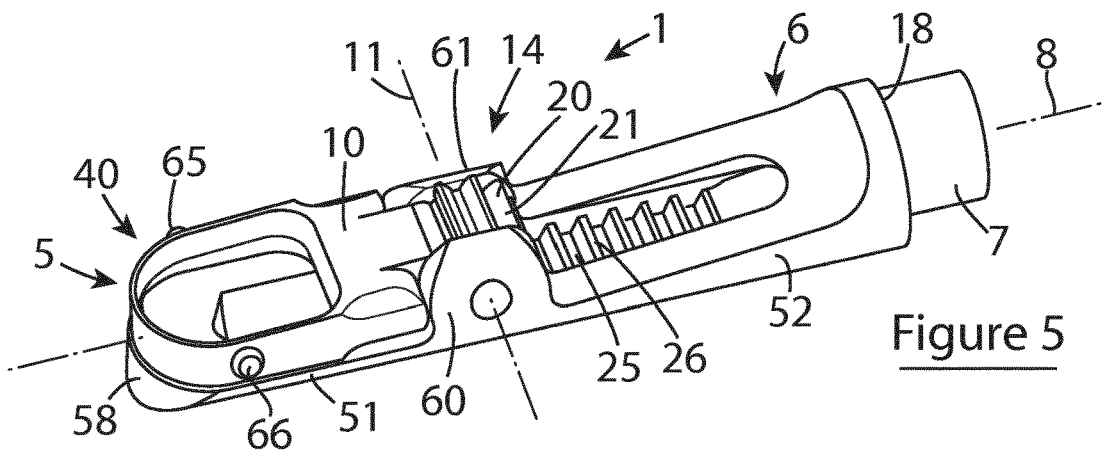
FIG. 5 shows an enlarged partial perspective view from one side of a releasably attachable surgical instrument head of a surgical cutting instrument of the type shown in FIG. 1 with a cutting arm pivoted at approximately 180 degrees relative to the position shown in FIG. 1.

The rotatable knob 16 is rotatable about the longitudinal axis 8 and it can be rotated clockwise and anticlockwise (as indicated by double-headed arrow A) to move the pivotal cutting arm 10 between the position shown in FIG. 2 and the position shown in FIG. 5 (and indeed to the other intermediate position shown in FIGS. 3, 4, 7 and 8). In use, a user rotating the knob 16 effects movement of the cutting arm 10, and can therefore resect tissue in a controlled manner. Again the knob can have a profile with a cross sectional area that is much greater than 7 mm.

A pinion 20 is integrally formed with the pivotal cutting arm 10. In the embodiment the pinion 20 has teeth 21 which extend sufficiently about one end of the arm 10 to allow the range of motion shown. As best seen from FIG. 12 the pinion is about two thirds of a complete pinion gear. It takes the form of a sector of a complete gear wheel.

A rack 25 with rack teeth 26 can be moved in a reciprocal linear motion forward towards the distal end 5 and rearwards toward the proximal end 6. The reciprocal linear motion is parallel to the longitudinal axis case of the instrument body 2. The rack teeth 26 of the rack 25, mesh with the pinion teeth 21 of the pinion 20. Accordingly the rack 25 and the pinion 20 thus mesh together to form a rack and pinion mechanism so that linear motion of the rack 25 effects pivotal movement of the pinion 20 and as it is a portion of the pivotal cutting arm 10 it effects pivotal movement of cutting arm 10 about the pivot axis 11. Rotation of the pinion 20 about the pivot axis 11, causes the pivot arm 10 to pivot relative to the instrument body 2.

The support 50 has an open top channel 55 defined therein. The rack 25 is located within the channel 25 and can be moved in a reciprocating linear motion forward towards the distal end 5 and rearwards toward the proximal end 4 within the channel 55. In the position of FIG. 2 the cutting arm 10 has been rotated rearwardly to abut the rearward support portion 52. In the position of FIG. 5 the cutting arm 10 has been rotated forwardly to abut the forward support portion 51. In other figures it is in a position intermediate those two positions.

Figure 6:
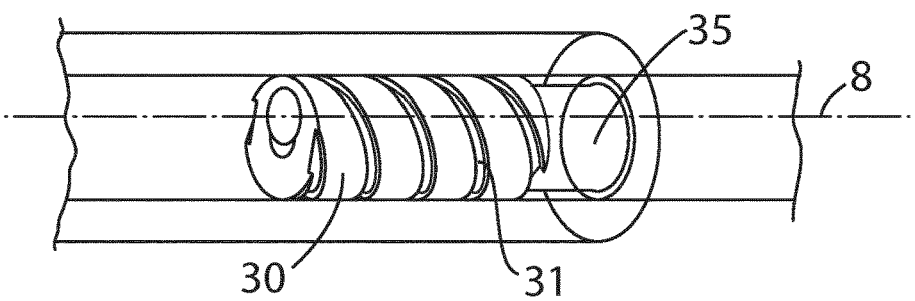
FIG. 6 shows an enlarged partial sectional view of a surgical cutting instrument of the type shown in FIG. 1 showing a worm screw forming part of a worm drive mechanism.

As best seen from FIG. 6 a worm screw 30 with (helical) worm screw teeth 31 effects reciprocal back and forth movement of the rack 25. A rotatable shaft 35 is provided which is freely rotatable within the hollow body 3. A proximal end of the shaft 35 is connected to the rotatable knob 16 so that rotation of the knob 16 rotates the rotatable shaft 35. The worm screw 30 is provided on a distal end of the rotatable shaft 35 so that rotation of the shaft by the knob 16 is transmitted to the worm screw teeth and in turn to the rack 25. The rack 25 then moves back or forth depending on the direction of rotation of the knob 16 and in turn rotates the pinion 20 and thus the cutting arm 10. The worm screw 30 thus meshes with the rack 25 so as to form a worm drive that effects movement of the rack 25.

The support portion 50 ends at the distal end 5 in a nose 58 which does not move with the cutting arm 10. Accordingly the nose 58 can be used to locate the surgical cutting instrument 1 of the invention by placing it in contact with a locating site within a body. For example, it could be pressed against the inside of a spinal disc and kept in this position while the cutting arm 10 is operated to cut through material within the spinal disc.

Figure 7:
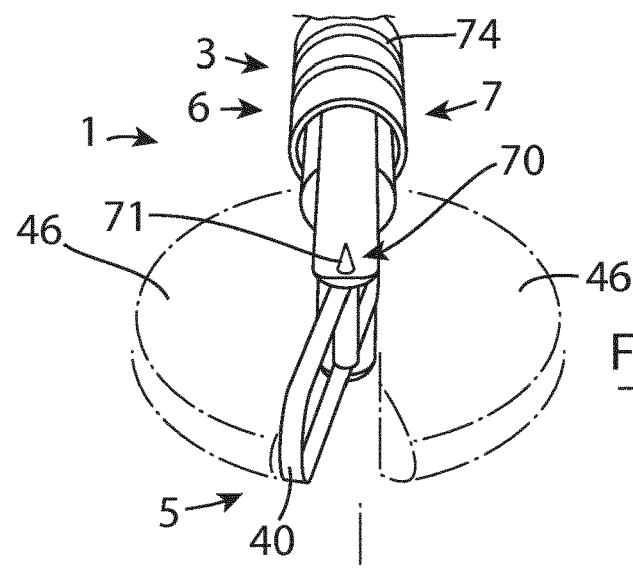
FIG. 7 shows an enlarged partial perspective view of a distal end of a surgical cutting instrument of the type shown in FIG. 1 with the device turned through 90 degrees.
Figure 8:
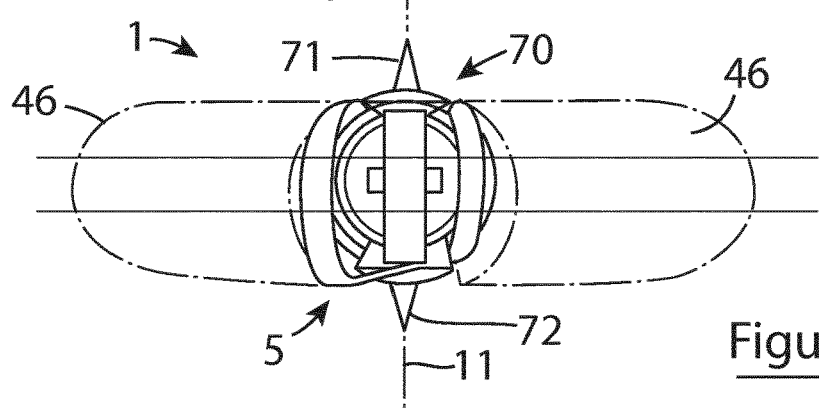
FIG. 8 is an end plan view of a distal end of a surgical cutting instrument of the type shown in FIG. 1 with the device in the same orientation as FIG. 7.
Figure 9:
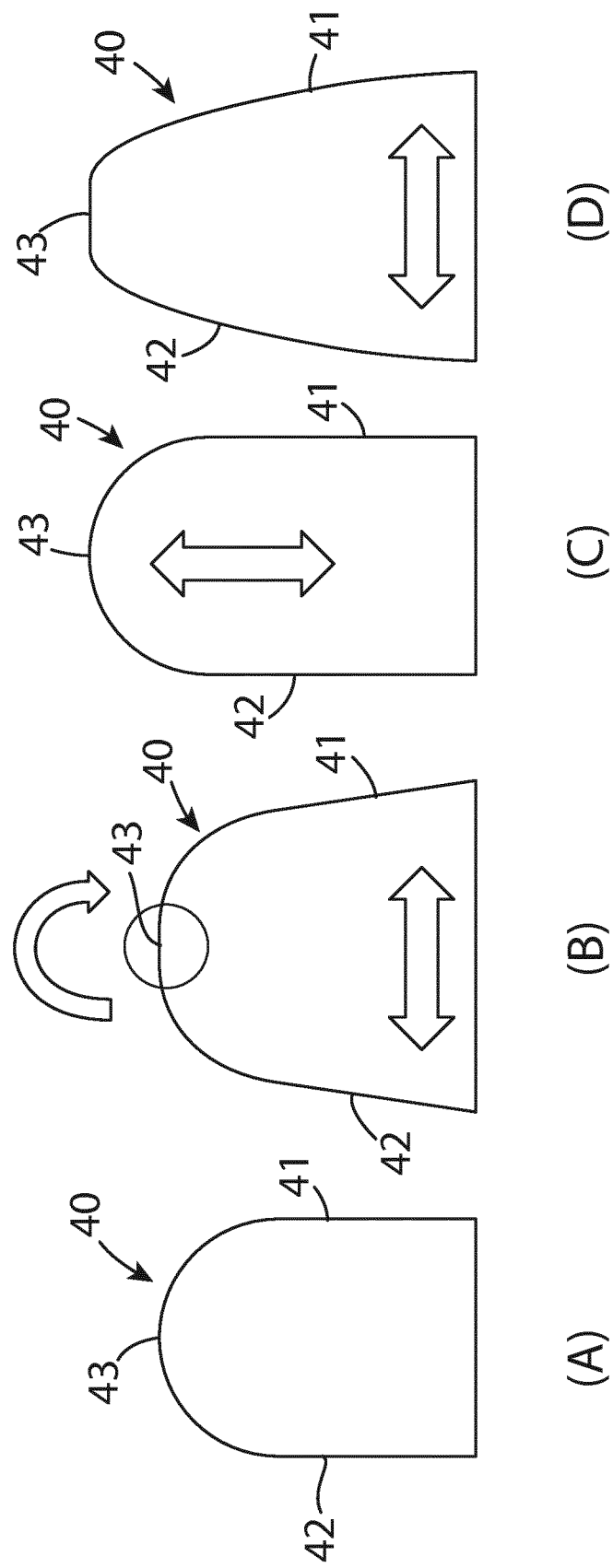
FIGS. 9(A) to 9(D) show schematic representations of various configurations of a u-shaped blade having two sides joined by a bridging portion and the bridging portion allows relative movement of the sides so that the shape of the blade is adjustable.

FIGS. 7 and 8 show the device of FIGS. 1 to 6 but this time rotated through 90 degrees about the longitudinal axis 8. By sweeping through the full pivotal range of movement of the cutting arm 10, and due to its shape the cutting blade 40 cuts out an ellipsoid like shape as indicated by the shape shown by broken lines which outline sections 46. It will be appreciated that other shapes of cutting arm/blades will cut out different shapes. It will be appreciated also that because of the u-shaped nature of the blade, the cutting arm cuts through and creates a block of cut-away material. The block of cut-away material can be removed by another surgical instrument such as a rongeur.

FIGS. 7, 8, 10 and 11 show a locating mechanism 70 for releasably locating the surgical cutting instrument 1 in place, when in use during surgery, relative to the anatomical part on which it is being used. For the purposes of illustration in this embodiment the support 50 is not shown in FIGS. 8 and 9. Also the blade 40 is shown without the protection runners 65, 66 in FIGS. 8 and 9.

Retractable locating pins 71,72 are provided and like the nose 58, can be placed in contact with a locating site within a body. They are placed in contact with a locating site within a body when they are in their working (non-retracted position). For example, the pins can be respectively located against upper and lower parts of the inside of a spinal disc (while the nose 58 is located against an internal side of the spinal disc,) and kept in this position while the cutting arm 10 is operated to cut through material within the spinal disc. When the surgical cutting instrument 1 is in use the pins can be extended for the purposes of securing the device in place. At times when the locating pins are not required they can be retracted. To maintain a low profile of a surgical cutting instrument of the invention it is desirable that the location mechanism, at least when in a retracted position, has a profile no greater than at least that part of the instrument body that is for insertion into a subject.

Figure 10:
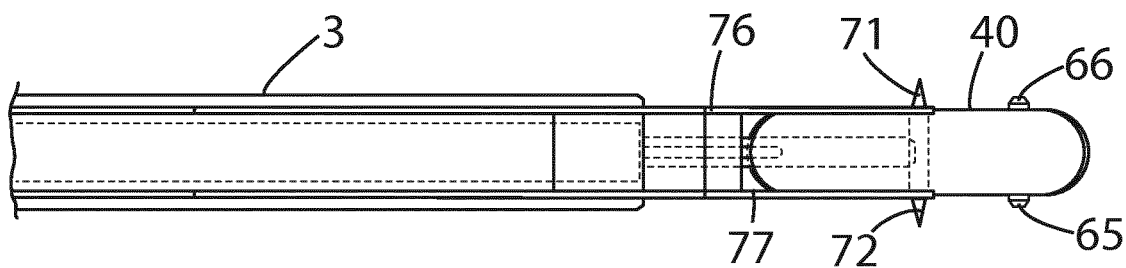
FIG. 10 is a schematic and partial sectional view of a part of a device of the invention showing a locating mechanism in a deployed or anchoring position.
Figure 11:
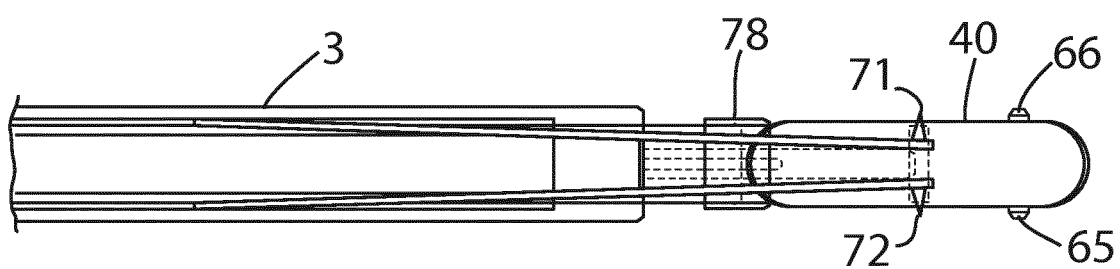
FIG. 11 is a schematic and partial sectional view of a part of the of FIG. 10 showing retraction of the locating mechanism.

The location mechanism includes a retracting mechanism. As is best seen in FIGS. 10 and 11 the pins 71,72 are located on resiliently deformable arms 76 and 77. For example the arms 76, 77 may be from a shape memory material. The arms can be brought together by sliding a slidable tube 78 along the arms to squeeze them together. To release them to the working or locating position this action is reversed. Movement of the slidable tube 78 can be effected from the grip 15.

For purposes of locating the surgical cutting instrument 1 of the present invention correctly at a target site, the surgical cutting instrument 1, for example the instrument body 2 thereof, can be provided with locating or indexing marks 74 (see FIG. 7) to assist in correct positioning. These indexing marks can be of a type visible to the naked eye and/or visible using imaging techniques such as fluoroscopy.

A surgical cutting instrument of the invention optionally further comprising a protection runner that moves with the cutting arm 10, so that in use it spaces the cutting blade 40 away from any surface the protection runner runs across. As best seen from FIG. 5 protection runners 65, 66 are provided on opposing outer sides of the cutting blade 40 so that the blade 40 is held away from a surface. The protection runners take the form of protrusions, in particular rounded protrusion protruding from an outer side of the blade. They are integrally formed with the blade. The protection runners 65,66 do not extend up to the cutting peripheral edges 43,44 of the blade 40 but rather are spaced to follow a distance from each cutting edge. Each protection runner 65,66 is spaced from both cutting edges and is equidistant from each and centred between them.

It is desirable that a surgical cutting instrument 1 of the present invention has a releasably attachable surgical instrument head 14 so that a first surgical instrument head can be swapped for another on the instrument body. For example the heads may be the same and they are swapped for the purposes of preventing cross contamination between uses. Alternatively, the heads may have different cutting arms and/or different cutting blades for different resection at different target sites. In the embodiments shown, the releasably attachable surgical instrument head 14 includes the pivotal cutting arm 10 which includes the pinion 20 and the cutting blade 40. Also it includes the support 50. So the cutting arm 10, the pinion 20, the cutting blade 40 and support 50 all form part of a releasably attachable surgical instrument head.

The releasably attachable surgical instrument head 14 separates from the remainder of the instrument body 2 along joint 18 (best seen in FIGS. 3-5 and 12).

Figure 12:
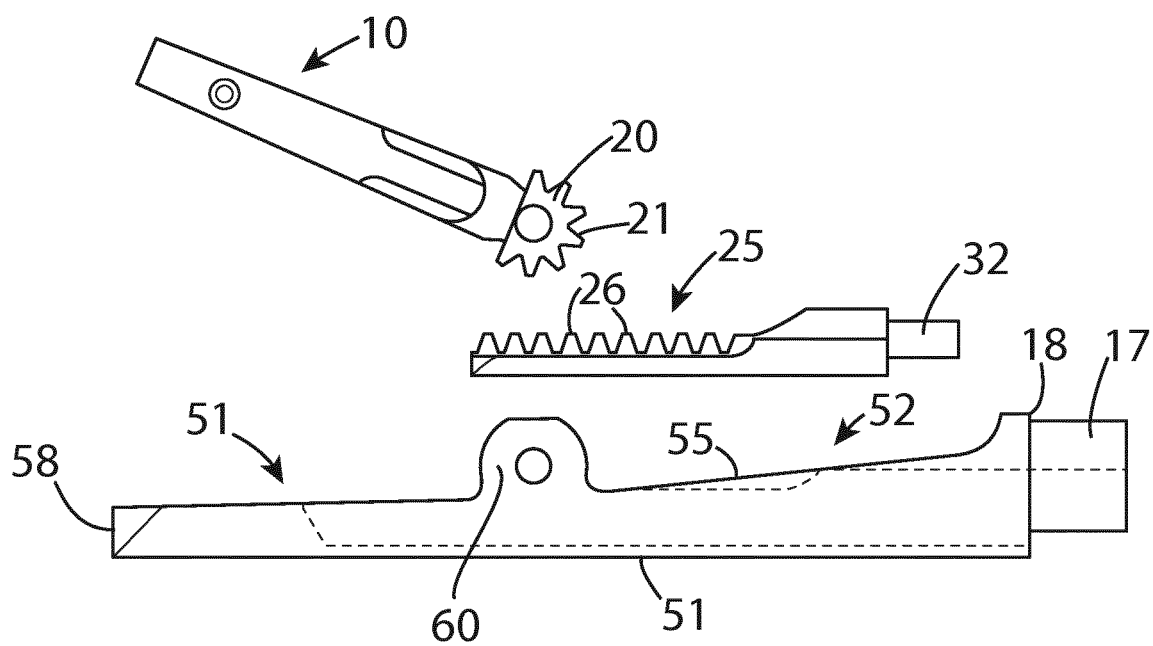
FIG. 12 is an exploded side view of a releasably attachable surgical instrument head of a surgical cutting instrument of the type shown in FIG. 1. It is noted that the drawings are shown in different scales in different figures.

The worm screw 30 is optionally removed with the removal of the releasably attachable surgical instrument head 14. Upon attaching the same or a new releasably attachable surgical instrument head 14 to the instrument body 2, the releasably attachable surgical instrument head 14 and the remainder of instrument body 2 automatically engage with each other. The rack 25 optionally comes off as part of the releasably attachable surgical instrument head 1. For example as shown in FIGS. 3,5 and 12 the releasably attachable surgical instrument head 14 may have a male part 17. For example as shown in FIG. 12 the worm screw 30 may have a male part 32. To connect the two parts together, the male part 17 of the releasably attachable surgical instrument head 14 is inserted within the elongate body 3 and they are then held together being separated by joint 18, optionally by automatic engagement with each other. As the two parts are connected together the male part 32 of the worm screw 40 automatically engages within shaft 35 optionally by automatic engagement with each other.

As can be seen from the figures, the surgical cutting instrument of the invention has a cutting arm can be rotated through at least 160 degrees for example about 180 degrees.

It will be appreciated that a surgical cutting instrument of the invention can be used to create a cut on one side thereof, and then it can be flipped over (for example through 180 degrees) to create a second cut which is continuous with the first. For example, to cut out an ellipsoid shape, the device of the invention is inserted in the configuration shown in FIG. 5. One the cutting arm 10 is located relative to the target site the knob 16 is rotated to rotate the cutting arm though substantially 180 degrees to the position shown in FIG. 2. This will cut out approximately one half of the ellipsoid shape. Thereafter, the entire device is flipped through 180 degrees and the process is repeated to cut out the remainder of the ellipsoid shape.

The shape cut out can remain and later be removed by a further surgical instrument.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A surgical cutting instrument having a proximal end, a distal end, opposing sides, and a longitudinal axis and comprising:
   (i) an instrument body;
   (ii) a pivotal cutting arm having a pinion with an axis of rotation, the pinion being integrally formed with the pivotal cutting arm, wherein the pivotal cutting arm is mounted for rotation relative to the instrument body about a pivot axis, the pivot axis being the axis of rotation of the pinion, so that, rotation of the pinion about the pivot axis, causes the pivot arm to pivot relative to the instrument body;
   (iii) a cutting blade on the pivotal cutting arm for resecting tissue wherein the cutting blade can cut when being moved in opposing rotational directions;
   (iv) a rack that can be moved in a reciprocating linear motion forward towards the distal end and rearwards toward the proximal end, the rack and the pinion being meshed together to form a rack and pinion mechanism so that linear motion of the rack effects pivotal movement of the pivotal cutting arm about the pivot axis and allows for cutting by the cutting blade in two opposing directions by rotation of the cutting arm in two opposing directions; and
   (v) a worm screw that meshes with the rack so as to form a worm drive that effects the reciprocating linear motion of the rack.

2. The surgical cutting instrument according to claim 1 wherein the cutting arm is pivotally mounted on a support which has a forward support portion which extends forwardly towards the distal end and a rearward support portion which extends rearwardly toward the proximal end.

3. The surgical cutting instrument according to claim 2 wherein the support has a channel defined therein and the rack can be moved in the reciprocating linear motion forward towards the distal end and rearwards toward the proximal end within the channel.

4. The surgical cutting instrument according to claim 2 wherein the cutting arm can be rotated about the pivot axis from a position in which it abuts the forward support portion to a position in which it abuts the rearward support portion.

5. The surgical cutting instrument according to claim 2 wherein the support has a channel defined therein, wherein the pivotal cutting arm is pivotally mounted to the instrument between two brackets located on the opposing sides of the instrument and the brackets are on opposite sides of the channel optionally wherein the rack can be moved in the reciprocating linear motion forward towards the distal end and rearwards toward the proximal end within the channel.

6. The surgical cutting instrument according to claim 1 wherein the pivotal cutting arm is pivotally mounted to the instrument between two brackets located on the opposing sides of the instrument.

7. The surgical cutting instrument according to claim 1 wherein the worm screw is at the end of a rotatable shaft.

8. The surgical cutting instrument according to claim 1 further comprising a locating mechanism for releasably locating the surgical cutting instrument in place, when in use during surgery, relative to an anatomical part on which it is being used.

9. The surgical cutting instrument according to claim 1 wherein the cutting blade is a u-shaped blade having two sides joined by a bridging portion and the bridging portion allows relative movement of the sides so that the shape of the blade is adjustable.

10. The surgical cutting instrument according to claim 1 further comprising a protection runner that moves with the cutting arm, so that in use it spaces the cutting blade away from any surface the protection runner runs across.

11. The surgical instrument according to claim 1 comprising a releasably attachable surgical instrument head so that a first surgical instrument head can be swapped for another on the instrument body.

12. The surgical instrument according to claim 11 wherein the first releasably attachable surgical instrument head comprises:
   (a) the pivotal cutting arm;
   (b) the pinion; and
   (c) the cutting blade.

13. The surgical instrument according to claim 11 wherein the releasably attachable surgical instrument head and the instrument body automatically engage with each other.

14. The surgical cutting instrument according to claim 1 wherein the cutting blade is a u-shaped blade.

15. The surgical cutting instrument according to claim 1, wherein the cutting arm can be rotated through at least 160 degrees for example about 180 degrees.

* * * * *